US011471440B2

(12) United States Patent
Kimura

(10) Patent No.: US 11,471,440 B2
(45) Date of Patent: *Oct. 18, 2022

(54) THERAPEUTIC AGENT FOR KERATOCONJUNCTIVE DISORDERS

(71) Applicant: YAMAGUCHI UNIVERSITY, Yamaguchi (JP)

(72) Inventor: Kazuhiro Kimura, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 13 days.

This patent is subject to a terminal disclaimer.

(21) Appl. No.: 16/700,866

(22) Filed: Dec. 2, 2019

(65) Prior Publication Data

US 2020/0345695 A1    Nov. 5, 2020

Related U.S. Application Data

(63) Continuation of application No. 16/008,730, filed on Jun. 14, 2018, now Pat. No. 10,537,556, which is a continuation of application No. 15/655,418, filed on Jul. 20, 2017, now Pat. No. 10,016,395, which is a continuation of application No. 15/293,548, filed on Oct. 14, 2016, now Pat. No. 9,750,721, which is a continuation of application No. 14/440,832, filed as application No. PCT/JP2013/006563 on Nov. 7, 2013, now Pat. No. 9,492,431.

(30) Foreign Application Priority Data

Nov. 8, 2012  (JP) ................................ 2012-246373

(51) Int. Cl.
| A61K 31/415 | (2006.01) |
| A61K 31/192 | (2006.01) |
| A61K 31/196 | (2006.01) |
| A61K 9/00 | (2006.01) |
| A61K 9/06 | (2006.01) |
| A61K 47/26 | (2006.01) |

(52) U.S. Cl.
CPC .......... *A61K 31/415* (2013.01); *A61K 9/0048* (2013.01); *A61K 9/06* (2013.01); *A61K 31/192* (2013.01); *A61K 31/196* (2013.01); *A61K 47/26* (2013.01)

(58) Field of Classification Search
None
See application file for complete search history.

(56) References Cited

U.S. PATENT DOCUMENTS

| 5,624,957 | A | 4/1997 | Swann et al. |
| 5,760,084 | A | 6/1998 | Swann et al. |
| 5,824,685 | A | 10/1998 | Campochiaro et al. |
| 6,075,032 | A | 6/2000 | Campochiaro et al. |
| 6,187,950 | B1 | 2/2001 | Song et al. |
| 6,204,288 | B1 | 3/2001 | Pershadsingh et al. |
| 6,313,168 | B1 | 11/2001 | Pacifici et al. |
| 6,777,418 | B2 | 8/2004 | Lapierre et al. |
| 6,838,472 | B2 | 1/2005 | Klaus et al. |
| 6,844,466 | B2 | 1/2005 | Belloni et al. |
| 7,345,931 | B2 | 3/2008 | Partsch et al. |
| 7,547,687 | B2 | 6/2009 | Reading et al. |
| 9,314,439 | B2 | 4/2016 | Iwamoto et al. |
| 9,492,431 | B2 | 11/2016 | Kimura |
| 9,750,721 | B2 | 9/2017 | Kimura |
| 10,016,395 | B2 * | 7/2018 | Kimura .................. A61P 27/02 |
| 10,537,556 | B2 * | 1/2020 | Kimura ................ A61K 9/0048 |
| 2002/0082265 | A1 | 6/2002 | Lapierre et al. |
| 2003/0113913 | A1 | 6/2003 | Purton et al. |
| 2003/0114482 | A1 | 6/2003 | Pacifici et al. |

(Continued)

FOREIGN PATENT DOCUMENTS

| CN | 1468207 A | 1/2004 |
| EP | 0747347 A1 | 12/1996 |

(Continued)

OTHER PUBLICATIONS

Acera et al., "Inflammatory Markers in the Tears of Patients with Ocular Surface Disease," Ophthalmic Res. 40(6):315-321 (2008).
Agadir et al., "Retinyl Methyl Ether Down-Regulates Activator Protein 1 Transcriptional Activation in Breast Cancer Cells," Cancer Research. 57(6):3444-50 (1997) (8 pages).
Araiz et al., "Antiproliferative Effect of Retinoic Acid in Intravitreous Silicone Oil in an Animal Model of Proliferative Vitreoretinopathy," Inv Ophthalmol & Vis Sci. 34(3):522-30 (1993).
Baudouin, "Un nouveau schéma pour mieux comprendre les maladies de la surface oculaire," J Fr. Ophthalmol. 30(3):239-246 (2007) (English abstract included).
Benkoussa et al., "Retinoic Acid Receptors Inhibit AP1 Activation by Regulating Extracellular Signal-Regulated Kinase and CBP Recruitment to an AP1-Responsive Promoter," Mol Cell Biol. 22(13):4522-34 (2002).

(Continued)

*Primary Examiner* — Michael Barker
(74) *Attorney, Agent, or Firm* — Clark & Elbing LLP

(57) ABSTRACT

The present invention addresses the problem of providing a novel therapeutic agent for keratoconjunctive disorders. As a means for solving the problem, a therapeutic agent for keratoconjunctive disorders which contains a RARγ agonist as an active ingredient is provided. The therapeutic agent exhibits an excellent ameliorating effect in a keratoconjunctive disorder model, and is therefore useful as a therapeutic agent for keratoconjunctive disorders such as corneal ulcer, corneal epithelial abrasion, keratitis, dry eye, conjunctivitis, chronic superficial keratitis, corneal erosion, persistent corneal disorders, superficial punctate keratopathy, corneal epithelial defects, conjunctival epithelial defects, keratoconjunctivitis sicca, superior limbic keratoconjunctivitis, filamentary keratoconjunctivitis, infectious keratitis, noninfectious keratitis, infectious conjunctivitis and noninfectious conjunctivitis. The therapeutic agent is also useful as a therapeutic agent for corneal scarring and conjunctival scarring both associated with keratoconjunctive disorders.

19 Claims, 6 Drawing Sheets

(56) References Cited

U.S. PATENT DOCUMENTS

| | | |
|---|---|---|
| 2003/0125252 A1 | 7/2003 | Underhill et al. |
| 2005/0271705 A1 | 12/2005 | Hughes et al. |
| 2006/0210638 A1 | 9/2006 | Liversidge et al. |
| 2009/0074789 A1 | 3/2009 | Sabbadini et al. |
| 2009/0176862 A1 | 7/2009 | Chandraratna et al. |
| 2009/0214493 A1 | 8/2009 | Pittenger et al. |
| 2009/0281184 A1 | 11/2009 | Sawada et al. |
| 2011/0076318 A1 | 3/2011 | Hughes et al. |
| 2012/0077786 A1 | 3/2012 | Byron et al. |
| 2013/0189319 A1 | 7/2013 | Cook et al. |
| 2014/0303223 A1 | 10/2014 | Iwamoto et al. |
| 2014/0363402 A1 | 12/2014 | Iwamoto et al. |
| 2015/0290172 A1 | 10/2015 | Kimura |
| 2016/0120843 A1 | 5/2016 | Kimura |
| 2017/0065562 A1 | 3/2017 | Kimura |

FOREIGN PATENT DOCUMENTS

| | | |
|---|---|---|
| EP | 1938815 A1 | 7/2008 |
| EP | 3000466 A1 | 3/2016 |
| JP | H08-333318 A | 12/1996 |
| JP | H11503998 A | 4/1999 |
| JP | 2004-510728 A | 4/2004 |
| JP | 2005-206544 A | 8/2005 |
| JP | 2007-535563 A | 12/2007 |
| JP | 4121552 B2 | 7/2008 |
| JP | 2009-235031 A | 10/2009 |
| JP | 2013-536855 A | 9/2013 |
| TW | 200538163 A | 12/2005 |
| WO | WO-94/15902 A1 | 7/1994 |
| WO | WO-01/80894 A2 | 11/2001 |
| WO | WO-2002/028810 A2 | 4/2002 |
| WO | WO-2005/107707 A1 | 11/2005 |
| WO | WO-2007/037188 A1 | 4/2007 |
| WO | WO-2007/113122 A1 | 10/2007 |
| WO | WO-2008/057930 A2 | 5/2008 |
| WO | WO-2010/071583 A1 | 6/2010 |
| WO | WO-2010/088735 A1 | 8/2010 |
| WO | WO-2012/030919 A2 | 3/2012 |
| WO | WO-2012/125724 A1 | 9/2012 |
| WO | WO-2012/129562 A2 | 9/2012 |
| WO | WO-2013/052647 A2 | 4/2013 |
| WO | WO-2014/073209 A1 | 5/2014 |
| WO | WO-2014/188716 A1 | 11/2014 |

OTHER PUBLICATIONS

Bergman et al., "Two improved and simplified methods for the spectrophotometric determination of hydroxyproline," Anal. Chem. 35(12):1961-5 (1963).
Bose et al., "Dry eye disease and uveitis: A closer look at immune mechanisms in animal models of two ocular autoimmune diseases," Autoimmun Rev. 15(12):1181-1192 (2016).
Caffery et al., "Ocular side effects of isotretinoin therapy," J Am Optom Assoc. 59(3):221-4 (1988) (Abstract Only).
Campochiaro, "Pathogenic Mechanisms in Proliferative Vitreoretinopathy," Arch Ophthalmol. 115(2):237-41 (1997).
Chang et al., "Effect of Oral 13-Cis-Retinoic Acid Treatment on Postoperative Clinical Outcome of Eyes With Proliferative Vitreoretinopathy," Am Journ Ophthalmol. 146(3):440-6 (2008) (8 pages).
Chen et al., "Transcriptional Regulation by Transforming Growth Factor beta of the Expression of Retinoic Acid and Retinoid X Receptor Genes in Osteoblastic Cells is Mediated through AP-1," Journ Biol Chem. 271(49):31602-6 (1996) (6 pages).
Chotikavanich et al., "Production and Activity of Matrix Metalloproteinase-9 on the Ocular Surface Increase in Dysfunctional Tear Syndrome," available in PMC Mar. 12, 2013, published in final edited form as: Invest Ophthalmol Vis Sci. 50(7):3203-3209 (2009) (18 pages).
Ciavarella et al., "20 novel point mutations and one large deletion in EXT1 and EXT2 genes: report of diagnostic screening in a large Italian cohort of patients affected by hereditary multiple exostosis," Gene. 515(2):339-48 (2013) (10 pages).
Communication pursuant to Article 94(3) EPC for European Patent Application No. 13854101.6, dated Jul. 26, 2018 (6 pages).
Corrales et al., "Desiccating Stress Stimulates Expression of Matrix Metalloproteinases by the Corneal Epithelium," Invest Ophthalmol Vis Sci.47(8):3293-3302 (2006).
Czajka et al., "What is the Proportion of Patients With Multiple Hereditary Exostoses Who Undergo Malignant Degeneration?" Clin Orthop Relat Res. 473(7):2355-61 (2015).
Danziger et al., "Automated site-directed drug design: a general algorithm for knowledge acquisition about hydrogen-bonding regions at protein surfaces," Proc R Soc Lond B Biol Sci. 236(1283):101-13 (1989).
De Paiva et al., "Corticosteroid and doxycycline suppress MMP-9 and inflammatory cytokine expression, MAPK activation in the corneal epithelium in experimental dry eye," Exp Eye Res. 83(3):526-535 (2006).
De Paiva et al., "Disruption of TGF-beta Signaling Improves Ocular Surface Epithelial Disease in Experimental Autoimmune Keratoconjunctivitis Sicca," PLoS One. 6(12):e29017 (2011) (9 pages).
Dedieu et al., "Retinoids interfere with the AP1 signalling pathway in human breast cancer cells," Cell Signal. 18(6):889-98 (2006).
Di Rocco et al., "Selective RAR gamma agonist blocks heterotopic ossification and promotes skeletal muscle repair," ASBMR Oct. 4, 2013, (Abstract only) (2 pages).
Di Rocco et al., "Selective retinoic acid receptor gamma agonists promote repair of injured skeletal muscle in mouse," Am J Pathol. 185(9):2495-504 (2015).
Du et al., "Retinoic acid suppresses the adhesion and migration of human retinal pigment epithelial cells," Exp Eye Res. 109:22-30 (2013).
Duncan et al., "The link between heparan sulfate and hereditary bone disease: finding a function for the EXT family of putative tumor suppressor proteins," J Clin Invest. 108(4):511-6 (2001).
Editors: Foulks et al. "2007 Report of the International Dry Eye Workshop (DEWS)," The Ocular Surface. 5(2):65-67; 69-193; 195-199; 202 (2007) (138 pages).
Einhorn et al., "Bone regeneration: new findings and potential clinical applications," J Am Acad Orthop Surg. 9(3):157-65 (2001).
English translation of Japanese Patent Application No. 2005-206544, dated Nov. 23, 2015 (14 pages).
English Translation of Office Action for Eurasian Patent Applicaiton No. 201370051, dated Jun. 1, 2015 (4 pages).
English Translation of Office Action for Israeli Patent Application No. 224973, dated Dec. 16, 2015 (2 pages).
Examination Report for Australian Patent Application No. 2015200760, dated Mar. 2, 2016 (4 pages).
Extended European Search Report for European Application No. 13854101.6, dated Apr. 19, 2016 (8 pages).
Extended European Search Report for European Application No. 18183955.6, dated Jan. 3, 2019 (9 pages).
Extended European Search Report for European Patent Application No. 11822537.4, dated Feb. 7, 2014 (10 pages).
Fanjul et al., "A new class of retinoids with selective inhibition of AP-1 inhibits proliferation," Nature. 372(6501):107-11 (1994).
Fekrat et al., "The Effect of Oral 13-cis-retinoic Acid on Retinal Redetachment after Surgical Repair in Eyes with Proliferative Vitreoretinopathy," Ophthalmol. 102(3):412-18 (1995).
First Examination Report for New Zealand Patent Application No. 706089, dated Mar. 25, 2015 (3 pages).
First Examination Report for New Zealand Patent Application No. 708756, dated Sep. 25, 2018 (3 pages).
Further Examination Report for New Zealand Patent Application No. 607547, dated Mar. 25, 2015 (2 pages).
Further Examination Report for New Zealand Patent Application No. 607547, dated Nov. 19, 2014 (2 pages).
Gayton, "Etiology, prevalence, and treatment of dry eye disease," Clin Ophthalmol. 3:405-12 (2009).
Giordano et al., "Sustained delivery of Retinoic Acid from Microspheres of Biodegradable Polymer in PVR," Inv Ophthalmol & Vis Sci. 34(9):2743-51 (1993).

(56) References Cited

OTHER PUBLICATIONS

Gollapalli et al., "The specific binding of retinoic acid to RPE65 and approaches to the treatment of macular degeneration," Proc Nat Acad Sci. 101(27):10030-5 (2004).
Halevy et al., "Retinoic acid induces adult muscle cell differentiation mediated by the retinoic acid receptor-alpha." J Cell Physiol. 154(3):566-72 (1993).
Hind et al., "Is a regenerative approach viable for the treatment of COPD?" Br J Pharmacol. 163(1):106-115 (2011).
Hu et al., "A novel retinoic acid analog, 4-amino-2-trifluoromethyl-phenyl retinate, inhibits gastric cancer cell growth," Int Journ Mol Med. 33(2):415-22 (2014).
Huang et al., "Retinoic Acid Actions Through Mammalian Nuclear Receptors," available in PMC on Jan. 8, 2015, published in final edited form as: Chem Rev. 114(1):233-54 (2014) (48 pages).
Huet et al., "EMMPRIN Modulates Epithelial Barrier Function through a MMP-Mediated Occludin Cleavage: Implications in Dry Eye Disease," Am J Pathol. 179(3):1278-1286 (2011).
International Preliminary Report on Patentability for International Application No. PCT/JP2014/002667, dated Dec. 1, 2014 (10 pages).
International Search Report and English Translation for International Patent Application No. PCT/2014/002667, dated Aug. 5, 2014 (5 pages).
International Search Report and English Translation for International Patent Application No. PCT/JP2013/006563, dated Dec. 10, 2013 (5 pages).
International Search Report for International Application No. PCT/US2011/049905, dated May 1, 2012 (4 pages).
Iwamoto et al., "Retinoic acid induces rapid mineralization and expression of mineralization-related genes in chondrocytes," Exp Cell Res 207(2): 413-420 (1993).
Japanese Office Action with English translation for Japanese Patent Application No. 2013-527250, dated Jul. 30, 2015 (6 pages).
Javadi et al., "Dry eye syndrome," J Ophthalmic Vis Res. 6(3):192-8 (2011).
Jo et al., "Establishment of a new animal model of focal subretinal fibrosis that resembles disciform lesion in advanced age-related macular degeneration," Invest Ophthalmol Vis Sci. 52(9):6089-95 (2011).
Jones et al., "Tesra (treatment of Emphysema with a selective retinoid agonist) study results," C91 Late Breaking Clinical Trials Symposium, May 17, Denver, CO. Am J Respir Crit Care Med. 183:A6418 (2011).
Junko et al., "38. Efficacy of retinoic acid receptor-specific agonist on choroidal neovascularization in mice," Research on Retinochoroidal and Optic Atrophy Heisei 15 Nendo Sokatsu 209-12 (2004) (8 pages).
Kaplan et al., "Derailing heterotopic ossification and RARing to go," Nat Med. 17(4):420-421 (2011).
Kennedy et al., "Retinoic acid enhances skeletal muscle progenitor formation and bypasses inhibition by bone morphogenetic protein 4 but not dominant negative beta-catenin," BMC Biol. 7:67 (2009). (21 pages).
Kim et al., "A comparison of vitamin a and cyclosporine a 0.05% eye drops for treatment of dry eye syndrome," Am J Ophthalmol. 147(2):206-13e2 (2009).
Kimura et al., "Suppression by an RAR-gamma Agonist of Collagen Degradation Mediated by Corneal Fibroblasts," Invest Ophthalmol Vis Sci. 58(4):2250-2257 (2017).
Kirchmeyer et al., "All-trans retinoic acid suppresses interleukin-6 expression in interleukin-1-stimulated synovial fibroblasts by inhibition of $ERK_{1/2}$ pathway independently of RAR activation," Arthritis Research. 10(6):R141 (2008)(12 pages).
Klaassen et al., "Metabolism and growth inhibition of four retinoids in head and neck squamous normal and malignant cells," Brit Journ Canc. 85(4):630-35 (2001).
Koyama et al., "Retinoid signaling is required for chondrocyte maturation and endochondral bone formation during limb skeletogenesis," Dev Biol. 208(2):375-91 (1999).

Krueger C et al., "Identification of Retinoic Acid in a High Content Screen for Agents that Overcome the Anti-Myogenic Effect of TGF-Beta-1," PLoS One 5(11): e15511 (2010) (11 pages).
Le May et al., Retinoid X Receptor Signalling in the Specification of Skeletal Muscle Lineage. *Skeletal Muscle—From Myogenesis to Clinical Relations*. Juliana Cseri, 49-72 (2012).
Lebowitz et al., "Ocular effects of oral retinoids," J Am Acad Dermatol. 19(1 Pt 2):209-11 (1988).
Lee et al., "Minocycline Controls Clinical Outcomes and Inflammatory Cytokines in Moderate and Severe Meibomian Gland Dysfunction," Am J Ophthalmol. 154(6):949-957 (2012).
Lefebvre et al., "Transcriptional Activities of Retinoic Acid Receptors," Vitamins and Hormones. 70:199-264 (2005).
Lemp, "Management of dry eye disease," Am J Manag Care. 14(3 Suppl):S88-101 (2008).
Liu et al., "All-trans-retinoic acid inhibition of transforming growth factor-beta-induced collagen gel contraction mediated by human Tenon fibroblasts: role of matrix metalloproteinases," Br J Ophthalmol. 99(4):561-65 (2015).
Luo et al., "Experimental Dry Eye Stimulates Production of Inflammatory Cytokines and MMP-9 and Activates MAPK Signaling Pathways on the Ocular Surface," Invest Ophthalmol Vis Sci. 45(12):4293-4301 (2004).
Matsumoto et al., "Conditional ablation of the heparan sulfate-synthesizing enzyme Ext1 leads to dysregulation of bone morphogenic protein signaling and severe skeletal defects," J Biol Chem. 285(25):19227-34 (2010).
Mori et al., "A Highly Soluble Matrix Metalloproteinase-9 Inhibitor for Potential Treatment of Dry Eye Syndrome," Basic Clin Pharmacol Toxicol. 111(5):289-295 (2012).
Nagano et al., "Stimulatory effect of pseudomonal elastase on collagen degradation by cultured keratocytes," Invest Ophthalmol Vis Sci. 42(6):1247-53 (2001).
Nagpal et al., "Separation of Transactivation and AP1 Antagonism Functions of Retinoic Acid Receptor alpha," Journ Bio Chem. 270(2):923-27 (1995).
Neuville et al., "Retinoic acid regulates arterial smooth muscle cell proliferation and phenotypic features in vivo and in vitro through an RARα-dependent signaling pathway." Arterioscler Thromb Vasc Biol. 19:1430-6 (1999).
Nezzar et al., "Molecular and metabolic retinoid pathways in the human ocular surface," Mol Vis. 13:1641-50 (2007).
Office Action and English Comments for Mexican Patent Application No. MX/a/2013/002275, dated Jan. 12, 2016 (8 pages).
Office Action and English Comments for Thai Patent Application No. 1301001049 (5 pages).
Office Action and its English translation for Chinese Patent Application No. 201180052926.X, dated May 8, 2014 (19 pages).
Office Action for U.S. Appl. No. 14/308,570, dated Jul. 31, 2014 (7 pages).
Pacifici et al., "Vitamin A inhibits chondrogenesis but not myogenesis," Exp Cell Res. 129(2):469-74 (1980) (Abstract Only).
Pacifici et al., Annual Report for U.S. Army Medical Research and Material Command, Oct. 2014, "Preventative Therapeutics for Heterotopic Ossification," (13 pages).
Pakala et al., "RAR gamma agonists inhibit proliferation of vascular smooth muscle cells," J Cardiovasc Pharmacol. 35(2):302-8 (2000) (Author manuscript) (17 pages).
Patent Examination Report No. 1 for New Zealand Patent Application No. 607547, dated Oct. 21, 2013 (3 pages).
Patent Examination Report No. 1 in Australian Patent Application No. 2011296080, dated Jul. 4, 2014 (4 pages).
Pfahl, "Nuclear Receptor/AP-1 Interaction," Endocrine Reviews. 14(5):651-8 (1993).
Pflugfelder et al., "Matrix Metalloproteinase-9 Knockout Confers Resistance to Corneal Epithelial Barrier Disruption in Experimental Dry Eye," Am J Pathol. 166(1):61-71 (2005).
Reichel et al., "New model of conjunctival scarring in the mouse eye," Br J Ophthalmol. 82(9):1072-1077 (1998).
Rhee, "Fibroblasts in three dimensional matrices: cell migration and matrix remodeling," Exp Mol Med. 41(12):858-65 (2009).

(56) References Cited

OTHER PUBLICATIONS

Rochette-Egly et al., "Dynamic and combinatorial control of gene expression by nuclear retinoic acid receptors (RARs)," Nuclear Receptor Signaling. 7:1-18 (2009).
Safran et al., Ocular Side Effects of Oral Treatment with Retinoids: A Review of Clinical Findings and Molecular Mechanisms, and a Prospective Study of the Influence of Acitretin on Retinal Function. *Retinoids: 10 Years On*. Saurat J-H, 315-326 (1991).
Sakimoto et al., "Metalloproteinases in Corneal Diseases: Degradation and Processing," Cornea. 31 Suppl 1(11):S50-6 (2012).
Samarawickrama et al., "Retinoic acid and the ocular surface," Surv Ophthalmol. 60(3):183-95 (2015).
Schadendorf et al., "Treatment of Melanoma Cells with the Synthetic Retinoid CD437 Induces Apoptosis via Activation of AP-1 In Vitro, and Causes Growth Inhibition in Xenografts In Vivo," Journ Cell Biol. 135(6):1889-98 (1996).
Schmale et al., "The natural history of hereditary multiple exostoses," J Bone Joint Surg Am. 76(7):986-92 (1994).
Schneider et al., "Activation of retinoic acid receptor alpha is sufficient for full induction of retinoid responses in SK-BR-3 and T47D human breast cancer cells," Cancer Res. 60(19):5479-87 (2000).
Seale et al., "The potential of muscle stem cells," Dev Cell. 1(3):333-42 (2001).
Second Office Action and English Comments for Chinese Patent Application No. 201180052926.X, dated Mar. 27, 2015 (12 pages).
Shimono et al., "A retinoid composition for rapid muscle repair and regeneration." Poster presented at BioTech 2010 Conference (Oct. 27, 2010).
Shimono et al., "Inhibition of ectopic bone formation by a selective retinoic acid receptor alpha-agonist: A new therapy for heterotopic ossification?," J Orthop Res. 28(2): 271-277 (2010).
Shimono et al., "Potent inhibition of heterotopic ossification by nuclear retinoic acid receptor-gamma agonists," Nat Med. 17(4):454-60 (2011).
Smith et al., "Tear film MMP accumulation and corneal disease," Br J Ophthalmol. 85(2):147-153 (2001).
Solomon et al., "Pro- and Anti-inflammatory Forms of Interleukin-1 in the Tear Fluid and Conjunctiva of Patients with Dry-Eye Disease," Invest Ophthalmol Vis Sci. 42(10):2283-2292 (2001).
Soprano et al., "Role of retinoic acid in the differentiation of embryonal carcinoma and embryonic stem cells." Vitam horm. 75:69-95 (2007).
Stern et al., "A unified theory of the role of the ocular surface in dry eye," Adv Exp Med Biol. 438:643-651 (1998).
Stern et al., "Autoimmunity at the ocular surface: pathogenesis and regulation," Mucosal Immunol. 3(5):425-442 (2010).
Stevenson et al., "Dry eye disease: an immune-mediated ocular surface disorder," available in PMC Jun. 10, 2013, published in final edited form as: Arch Ophthalmol. 130(1):90-100 (2012) (19 pages).
Stolk et al., "Randomised controlled trial for emphysema with a selective agonist of the gamma-type retinoic acid receptor," Eur Respir J. 40(2):306-12 (2012).
Stolk et al., "Retinoid treatment of Emphysema in Patients on the Alpha-1 International Registry. The REPAIR study: study design, methodology and quality control of study assessments," Ther Adv Respir Dis. 4(6):319-32 (2010).
Sun et al., "Induction of Apoptosis in Human Non-Small Cell Lung Carcinoma Cells by the Novel Synthetic Retinoid CD437," J Cell Phys. 173(2):279-284 (1997).
Sun et al., "The synthetic retinoid CD437 selectively induces apoptosis in human lung cancer cells while sparing normal human lung epithelial cells," Cancer Res. 62(8):2430-6 (2002).
Thacher et al., "Therapeutic applications for ligands of retinoid receptors," Curr Pharm Des. 6(1):25-58 (2000).
Third Office Action and English Comments for Chinese Patent Application No. 201180052926.X, dated Oct. 12, 2015 (11 pages).
Tsai et al., "Extracellular Signals Regulate Rapid Coactivator Recruitment at AP-1 Sites by Altered Phosphorylation of both CREB Binding Protein and c-jun," Mol Cell Biol. 28(13):4240-50 (2008).
Tseng et al., "Topical retinoid treatment for various dry-eye disorders," Ophthalmology 92(6):717-27 (1985).
Veloso Jr. et al., "13-cis-Retinoic Acid in Silicone-Fluorosilicone Copolymer Oil in a Rabbit Model of Proliferative Vitreoretinopathy," Exp Eye Res. 65(3):425-34 (1997).
Vincenti et al., "v-src Activation of the Collagenase-1 (Matrix Metalloproteinase-1) Promoter through PEA3 and STAT: Requirement of Extracellular Signal-Regulated Kinases and Inhibition by Retinoic Acid Receptors," Mol Carc. 21(3):194-204 (1998).
Weston et al., "Requirement for RAR-mediated gene repression in skeletal progenitor differentiation," J Cell Biol. 158(1):39-51 (2002).
Weston et al., "Revisiting the role of retinoid signaling in skeletal development," Birth Defects Res C Embryo Today. 69(2):156-73 (2003).
Widschwendter et al., "Activity of Retinoic Acid Receptor-gamma Selectively Binding Retinoids Alone and in Combination with Interferon-gamma in Breast Cancer Cell Lines," Int J Cancer. 71(3):497-504 (1997).
Williams et al., "Retinoic acid receptors are required for skeletal growth, matrix homeostasis and growth plate function in postnatal mouse," Dev Biol. 328(2):315-27 (2009).
Wozney et al., "Novel regulators of bone formation: molecular clones and activities," Science. 242(4885):1528-34 (1988).
Wu et al., "Effects of Retinoic Acid on Retinal Pigment Epithelium from Excised Membranes from Proliferative Vitreoretinopathy," Journ Ocul Pharm Ther. 21(1):44-54 (2004) (12 pages).
Wuyts et al., "Hereditary Multiple Osteochondromas," GeneReviews, posted Aug. 3, 2000, last updated Nov. 21, 2013 (17 pages).
Yan et al., "Antiproliferative effect of sustained drug delivery system of all-trans retinoic acid implant into rabbit's vitreous cavity for treatment of proliferative vitreoretinopathy," Zhonghua Yan Ke Za Zhi. 39(10):621-5 (2003) (Abstract Only).
Yasuhara et al. "Wnt/beta-catenin and retinoic acid receptor signaling pathways interact to regulate chondrocyte function and matrix turnover." J Biol Chem. 285(1):317-327 (2010).
Yasunari et al., "Effect of Retinoic Acid on Proliferation and Polyamine Metabolism in Cultured Bovine Retinal Pigment Epithelial Cells," Ophthalmic Res. 31(1):24-32 (1999).
Zasloff et al., "Treatment of patients who have fibrodysplasia ossificans progressiva with isotretinoin," Clin Orthop Relat Res. 346:121-9 (1998).
Araya et al., "The Novel Formulation Design of Self-emulsifying Drug Delivery Systems (SEDDS) Type O/W Microemulsion II: Stable Gastrointestinal Absorption of a Poorly Water Soluble New Compound, ER-1258 in Bile-fistula Rats," Drug Metab Pharmacokinet. 20(4):257-67 (2005).

\* cited by examiner

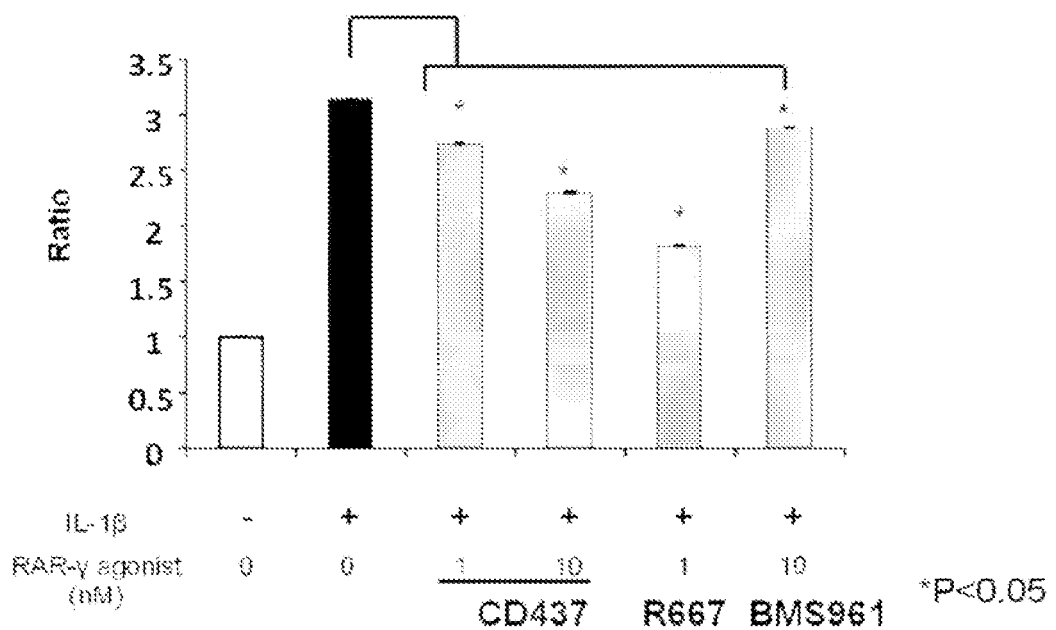

THERAPEUTIC AGENT FOR KERATOCONJUNCTIVE DISORDERS

TECHNICAL FIELD

The present invention relates to a therapeutic agent for a keratoconjunctive disorder containing a RARγ agonist as an effective ingredient.

BACKGROUND ART

The cornea is a transparent avascular tissue with a diameter of about 1 cm, covering the front surface of an eye ball. The conjunctiva is a mucous membrane covering the back surface of the eye lid and the surface of an eye ball which is posterior to the corneal limbus. The cornea and the conjunctiva serve an important role in vision. It is known that visual function is seriously affected when a disorder occurs therein. Keratoconjunctive disorders induced by various diseases such as corneal ulcer, keratitis, and dry eye are disorders caused by a delay in recovery from a disorder due to some reason such as an external injury or by a disorder that has become chronic. Since the cornea is a tissue that is connected to the conjunctiva, such diseases negatively affect each other in the normal construction of the epithelium and in some cases harm the structure or functioning of the corneal stroma or endothelium.

Collagen (especially type I collagen) is known as one of the representative stromal components of corneal parenchymal tissue. A functional disorder resulting from stromal degradation occurs in diseases due to a keratoconjunctive disorder. Thus, suppression of degradation of collagen (especially type I collagen) is considered effective against diseases caused by a keratoconjunctive disorder.

In a keratoconjunctive disorder, scar tissue, which is often formed after an inflammation has calmed, may obstruct the visual function. For this reason, suppression of collagen contraction, if possible, is considered effective against contraction and formation of scars (hereinafter, referred together as "scar formation") as in the above-described suppression of collagen degradation.

Patent Literature 1 describes that all-trans retinoic acid (hereinafter, also referred to as ATRA) promotes corneal regeneration. However, the effect thereof is weak and the detailed mechanism thereof is yet to be elucidated.

Further, ATRA is an agonist of retinoic acid receptors (hereinafter, also referred to as RAR). However, since ATRA does not have selectivity with respect to RAR subtypes RARα, RARβ, and RARγ, the contribution of each RAR subtype to corneal regeneration effects is unknown.

Meanwhile, RAR is involved in various effects such as growth, morphogenesis and differentiation in many cells, such as inflammatory cells, immune cells, and structural cells. Further, it is verified that there is a difference in the distribution of RAR subtypes depending on the tissue or organ of a mammal.

Some of the effects of RAR are undesirable, such as increase in triglyceride due to RARα. Thus, the specificity or selectivity with respect to subtypes in compounds with RAR agonist activity is expected to lead to reduction in risk of side effects.

For the above reasons, there is a demand for RAR agonists, which have a strong effect of suppressing keratoconjunctive disorders and are highly safe based on subtype selectivity.

Patent Literatures 2 and 3 disclose the RAR agonist (E)-4-(2-{3-[(1H-pyrazole-1-yl)methyl]-5,5,8,8-tetramethyl-5,6,7,8-tetrahydronaphthalene-2-yl}vinyl)benzoic acid and the derivatives thereof. Further, Patent Literature 2 describes that (E)-4-(2-{3-[(1H-pyrazole-1-yl)methyl]-5,5,8,8-tetramethyl-5,6,7,8-tetrahydronaphthalene-2-yl}vinyl)benzoic acid is useful against pulmonary emphysema, cancer, and dermatosis. Patent Literature 3 describes that the above-described agonist is useful against neurological pain.

In addition, Non-Patent Literature 1 describes that the RAR agonist 6-[3-(1-adamantyl)-4-hydroxyphenyl]-2-naphthalene acid induces apoptosis in lung cancer cells.

Furthermore, Patent Literature 4 describes that the RAR agonist 3-fluoro-4-[2-hydroxy-2-(5,5,8,8-tetramethyl-5,6,7,8-tetrahydronaphthalene-2-yl)acetylamino]benzoic acid is useful in muscle repair or regeneration.

However, pharmacological effects on keratoconjunctive disorders or scar formation resulting from keratoconjunctive disorders are not discussed or reported for any of the RAR agonists. In addition, there is no literature that suggests such an effect.

CITATION LIST

Patent Literature

[PTL 1] Japanese Laid-Open Publication No. 2009-235031
[PTL 2] International Publication No. WO 2002/028810
[PTL 3] International Publication No. WO 2008/057930
[PTL 4] Japanese Laid-Open Publication No. 2013-536855

Non Patent Literature

[NPL 1] Sun S Y et al., Cancer Research 62(8): 2430-2436 (2002)

SUMMARY OF INVENTION

Technical Problem

The search for a drug that is effective against ophthalmic diseases, especially keratoconjunctive disorders, is an objective that is important and of interest. The objective of the present invention is to provide a therapeutic agent that has an effect of suppressing a keratoconjunctive disorder and is highly safe based on subtype selectivity.

Solution to Problem

After diligent research to find a drug that is effective against keratoconjunctive disorders, the inventors discovered that the RARγ agonist (E)-4-(2-{3-[(1H-pyrazole-1-yl)methyl]-5,5,8,8-tetramethyl-5,6,7,8-tetrahydronaphthalene-2-yl}vinyl)benzoic acid (R667: hereinafter, also referred to as "RARγ agonist A") exerts an excellent effect of ameliorating keratoconjunctive disorders as well as scar formation associated with keratoconjunctive disorders by pharmacological tests using rabbit keratocytes and subconjunctival fibroblasts, wherein a potent effect of suppressing collagen degradation as well as a significant effect of suppressing collagen contraction were demonstrated. Furthermore, it was discovered that other RARγ agonists, 6-[3-(1-adamantyl)-4-hydroxyphenyl]-2-naphthalene acid (CD437: hereinafter, also referred to as "RARγ agonist B") and 3-fluoro-4-[2-hydroxy-2-(5,5,8,8-tetramethyl-5,6,7,8-tetrahydronaphthalene-2-yl)acetylamino]benzoic acid (BMS961: hereinafter, also referred to as "RARγ agonist C") also exhibit a significant effect of suppressing collagen degradation in pharmacological tests using rabbit keratocytes to complete the present invention.

Specifically, the present invention is [1] a therapeutic agent for a keratoconjunctive disorder, comprising a RARγ agonist as an effective ingredient, [2] the therapeutic agent of the above-described [1], wherein the RARγ agonist is (E)-4-(2-{3-[(1H-pyrazole-1-yl)methyl]-5,5,8,8-tetramethyl-5,6,7,8-tetrahydronaphthalene-2-yl}vin yl)benzoic acid, 6-[3-(1-adamantyl)-4-hydroxyphenyl]-2-naphthalene acid, 3-fluoro-4-[2-hydroxy-2-(5,5,8,8-tetramethyl-5,6,7,8-tetrahydronaphthalene-2-yl)acetylamino]benzoic acid, an ester thereof, or a salt thereof, [3] the therapeutic agent of above-described [1] or [2], wherein the keratoconjunctive disorder is selected from the group consisting of corneal ulcer, corneal epithelial abrasion, keratitis, dry eye, conjunctivitis, chronic superficial keratitis, corneal erosion, persistent corneal disorders, superficial punctate keratopathy, corneal epithelial defects, conjunctival epithelial defects, keratoconjunctivitis sicca, superior limbic keratoconjunctivitis, filamentary keratoconjunctivitis, infectious keratitis, noninfectious keratitis, infectious conjunctivitis, noninfectious conjunctivitis, corneal cicatrization, and conjunctival cicatrization, [4] the therapeutic agent according to any one of the above-described [1]-[3], wherein a form of administration is instillative administration or oral administration, and [5] the therapeutic agent accordingly to any one of the above-described [1]-[4], wherein a dosage form is an instillation, an ophthalmic ointment, an injection, a tablet, a granule, a fine granule, a powder or a capsule.

Advantageous Effects of Invention

RARγ agonists, which are effective ingredients of the therapeutic agent for a keratoconjunctive disorder of the present invention, are useful as a therapeutic agent for keratoconjunctive disorders, such as corneal ulcer, corneal epithelial abrasion, keratitis, dry eye, conjunctivitis, chronic superficial keratitis, corneal erosion, persistent corneal disorders, superficial punctate keratopathy, corneal epithelial defects, conjunctival epithelial defects, keratoconjunctivitis sicca, superior limbic keratoconjunctivitis, filamentary keratoconjunctivitis, infectious keratitis, noninfectious keratitis, infectious conjunctivitis or noninfectious conjunctivitis, by strongly suppressing keratoconjunctive collagen degradation.

Further, RARγ agonists, which are effective ingredients of the therapeutic agent for a keratoconjunctive disorder of the present invention, are also useful as a therapeutic agent for corneal cicatrization or conjunctival cicatrization associated with a keratoconjunctive disorder by strongly suppressing keratoconjunctive collagen contraction.

BRIEF DESCRIPTION OF DRAWINGS

FIG. 4 is a graph showing the relationship of the concentrations (nM) of RARγ agonist A (R667), RARγ agonist B (CD437), and RARγ agonist C (BMS961) with respect to collagen degradation, when using keratocytes. The vertical axis represents the ratio (Ratio) of the amount (μg) of hydroxyproline per well when a RARγ agonist and a stimulant are added, in cases where the amount (μg) of hydroxyproline per well when a RARγ agonist and a stimulant are not added is set to 1, wherein "*" indicates the presence of a statistically significant difference ($p<0.05$).

FIG. 5B shows the expression and activation of MMP-2 and MMP-9. FIGS. 6A and 6B show the results of observation when a lipopolysaccharide (LPS) and a RARγ agonist A (R667) are administered into the corneal stroma in one eye of male Japanese white rabbits. The top row (FIG. 6A) (Vehicle) is the result of administering only a solution that does not contain the RARγ agonist A (R667) of the present invention, and the bottom row (FIG. 6B) (0.1% R667) is the result of administering a solution containing RARγ agonist A (R667).

DESCRIPTION OF EMBODIMENTS

Figure 1:
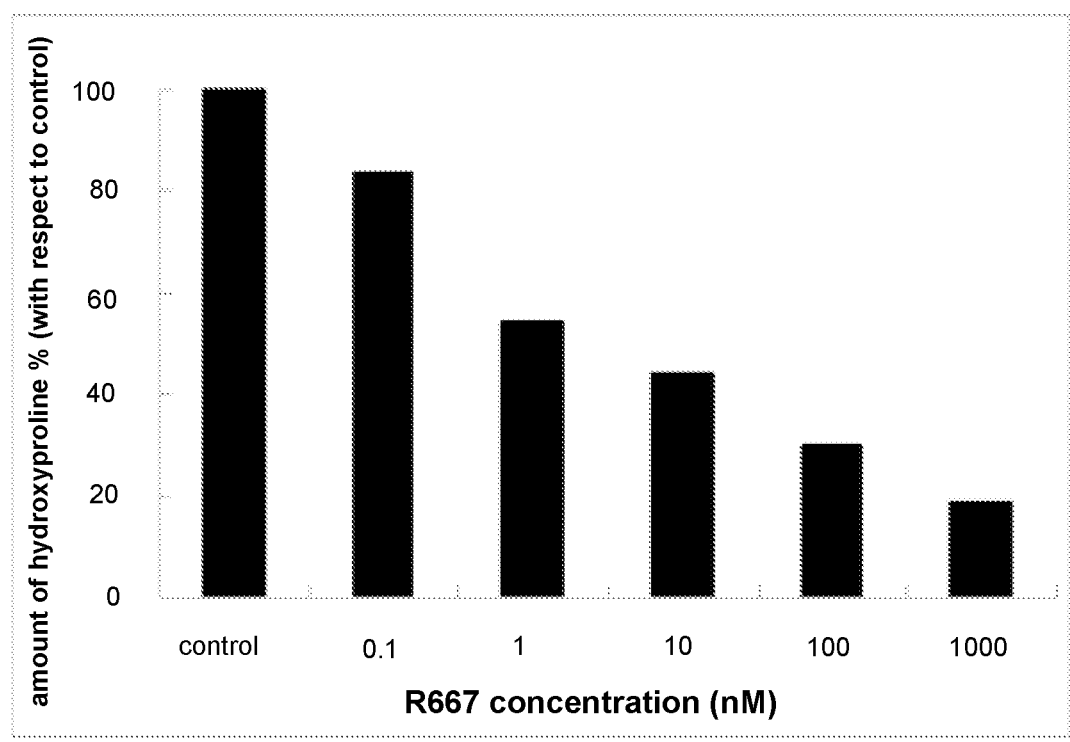
FIG. 1 is a graph showing the relationship between the concentration (nM) of RARγ agonist A (R667) and collagen degradation (amount (μg) of hydroxyproline per well). The vertical axis represents the numerical value (%) when the amount of hydroxyproline of the control is set to 100.

The therapeutic agent for a keratoconjunctive disorder of the present invention is not particularly limited and may be any therapeutic agent having a RARγ agonist as the effective ingredient. The RARγ agonist of the present invention refers to a compound that can promote the activation of a RARγ receptor by binding to a RARγ receptor significantly in comparison to RAR a receptors or RAR 13 receptors.

Examples of such RARγ agonists include (E)-4-(2-{3-[(1H-pyrazole-1-yl)methyl]-5,5,8,8-tetramethyl-5,6,7,8-tetrahydronaphthalene-2-yl}vin yl)benzoic acid (R667) represented by the following formula (I), 6-[3-(1-adamantyl)-4-hydroxyphenyl]-2-naphthalene acid (CD437) represented by the following formula (II), 3-fluoro-4-[2-hydroxy-2-(5,5,8,8-tetramethyl-5,6,7,8-tetrahydronaphthalene-2-yl)acetylamino]benzoic acid (BMS961) represented by the following formula (III), (2E)-3-(4-carboxyphenyl)-1-(5,5,8,8-tetramethyl-5,6,7,8-tetrahydronaphthalene-2-yl)-2-propene-1-one oxime (NRX204647: hereinafter, also referred to as "RARγ agonist D") represented by the following formula (IV), 4-[7-(1-adamantyl)-6-hydroxynaphthalene-2-yl] benzoic acid (CD1530: hereinafter, also referred to as "RARγ agonist E") represented by the following formula (V), esters of such compounds (RARγ agonists A, B, C, D, and E), and salts of such compounds (RARγ agonists A, B, C, D, and E). Preferred examples of RARγ agonists include RARγ agonist A, RARγ agonist B, RARγ agonist C, esters of such compounds (RARγ agonists A, B, and C), and salts of such compounds (RARγ agonists A, B, and C).

[Chemical 1]

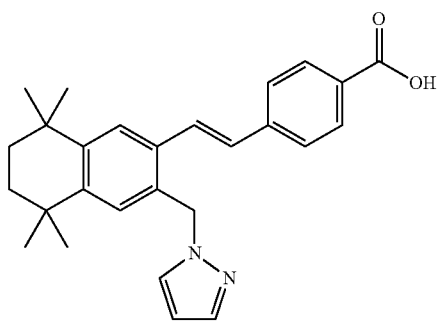

(I)

[Chemical 2]

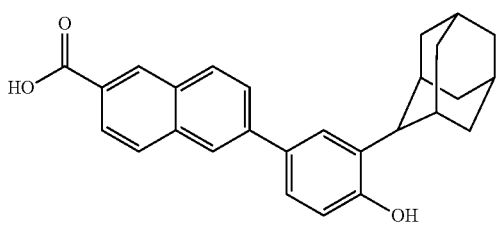

(II)

[Chemical 3]

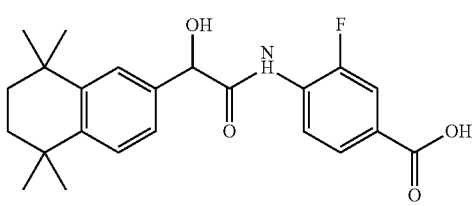

(III)

[Chemical 4]

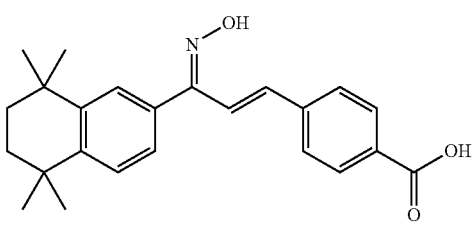

(IV)

[Chemical 5]

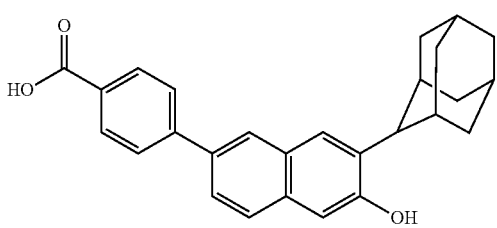

(V)

Further, other embodiments of the present invention include a method of treating a keratoconjunctive disorder characterized by administering the RARγ agonist of the present invention to a subject, a RARγ agonist of the present invention for use as a therapeutic agent for a keratoconjunctive disorder, and use of the RARγ agonist of the present invention in the preparation of a therapeutic agent for a keratoconjunctive disorder.

RARγ agonist A, which is one of the effective ingredients of the therapeutic agent for a keratoconjunctive disorder of the present invention, an ester thereof and a salt thereof are known compounds described in Patent Literature 2. They can be manufactured in accordance with the method described in Patent Literature 2 or purchased as a commercially-available product. Examples of the commercially-available products include product name: palovarotene manufactured by Shanghai Haoyuan Chemexpress.

Among the effective ingredients of the therapeutic agents for a keratoconjunctive disorder of the present invention, RARγ agonist B is a known compound described in Non-Patent Literature 1 and Patent Literature 4, RARγ agonist C is a known compound described in Patent Literature 4, and RARγ agonists D and E are known compounds described in the following document (Shimono K. et al., Nat Med. 17(4): 454-460 (2011)). Said compounds, esters thereof and salts thereof can be manufactured in accordance with a conventional method or purchased as a commercially-available product. Examples of commercially available products include product name: CD437 (ab141305) manufactured by Abcam and product name: CD437 manufactured by Tocris Bioscience for RARγ agonist B, product name: BMS961 manufactured by Tocris Bioscience for RARγ agonist C, and product name: CD1530 manufactured by Santa Cruz biotechnology and product name: CD1530 manufactured by Tocris Bioscience for RARγ agonist E.

Esters in the aforementioned esters of RARγ agonists A, B, C, D, and E, which are effective ingredients of the therapeutic agent for a keratoconjunctive disorder of the present invention, are not particularly limited and may be any ester converted to RARγ agonists A, B, C, D, or E in a reaction by an enzyme or the like under physiological conditions in vivo. Such esters include: esters generated by reaction with a primary alcohol, such as methanol, ethanol, propanol, hexanol, or dodecanol; esters generated by reaction with a secondary alcohol such as isopropanol, s-butanol, or 1-ethylpropanol; esters generated by reaction with a tertiary alcohol such as t-butanol or 1-methyl-1-ethylpropanol; and esters generated by reaction with an amino alcohol such as 2-aminoethanol.

The above-described esters can be manufactured by a known method from the aforementioned RARγ agonists A, B, C, D, E, or a synthetic intermediate thereof.

Salts in the aforementioned salts of RARγ agonists A, B, C, D, and E, which are effective ingredients of the therapeutic agent for a keratoconjunctive disorder of the present invention, are not particularly limited and may be any pharmaceutically acceptable salts. Such salts include (1) as an acid addition salt, inorganic acid salts such as hydrochloride, hydrobromic acid salt, hydroiodic acid salt, nitric acid salt, sulfuric acid salt, and phosphoric acid salt; and organic acid salts such as acetic acid salt, trifluoroacetic acid salt, benzoic acid salt, oxalic acid salt, malonic acid salt, succinic acid salt, maleic acid salt, fumaric acid salt, tartaric acid salt, citric acid salt, methanesulfonic acid salt, ethanesulfonic acid salt, trifluoromethanesulfonic acid salt, benzenesulfonic acid salt, p-toluenesulfonic acid salt, glutamic acid salt, and aspartic acid salt and (2) as a basic salt, metal salts such as sodium salt, potassium salt, calcium salt and magnesium salt; inorganic salts such as ammonium salt; and organic amine salts such as triethylamine salt and guanidine salt.

In the present invention, a keratoconjunctive disorder refers to a condition where a cornea or a conjunctiva is damaged due to various factors such as an abnormality in lacrimal fluid, metabolic abnormality, or external injury. Examples thereof include corneal ulcer, corneal epithelial abrasion, keratitis, dry eye, conjunctivitis, chronic superficial keratitis, corneal erosion, persistent corneal disorders, superficial punctate keratopathy, corneal epithelial defects, conjunctival epithelial defects, keratoconjunctivitis sicca, superior limbic keratoconjunctivitis, filamentary keratoconjunctivitis, infectious keratitis, noninfectious keratitis, infectious conjunctivitis and noninfectious conjunctivitis. Suppressing action on collagen degradation exerts an excellent ameliorating effect. Further, in the present invention, corneal cicatrization (scar formation on the cornea) and conjunctival cicatrization (scar formation on the conjunctiva) associated with a keratoconjunctive disorder are also examples of keratoconjunctive disorders. Suppressing action on collagen contraction exerts an excellent ameliorating effect.

The therapeutic agent for a keratoconjunctive disorder of the present invention can be administered orally or parenterally (intravenous administration, intramuscular administration, intraperitoneal administration, percutaneous administration, intratracheal administration, intracutaneous administration, or subcutaneous administration) in a form of a tablet, capsule, powder, syrup, granule, fine granule, pill, liquid formulation, suspension, emulsion, percutaneous absorption agent, suppository, ointment (preferably ophthalmic ointment), lotion, inhalant, or injection manufactured by mixing in a suitable pharmacologically acceptable additive.

These formulations are manufactured by a well-known method by using an additive such as an excipient, lubricant, binding agent, disintegrator, emulsifier, stabilizer, flavoring agent or diluent.

Examples of excipients include organic excipients and inorganic excipients. Examples of organic excipients include: sugar derivatives such as lactose, sucrose, glucose, mannitol, and sorbitol; starch derivatives such as corn starch, potato starch, α-starch and dextrin; cellulose derivatives such as crystalline cellulose; gum arabic; dextran; and pullulan. Examples of inorganic excipients include: light anhydrous silicic acid; and sulfuric acid salts such as calcium sulfate.

Examples of lubricants include: stearic acid; metal salts of stearic acid such as calcium stearate and magnesium stearate; talc; colloidal silica; wax such as beeswax and spermaceti; boric acid; adipic acid; sulfuric acid salts such as sodium sulfate; glycol; fumaric acid; sodium benzoate; D,L-Leucine, sodium lauryl sulfate; silicic acids such as silica and silicic acid hydrate; and the starch derivatives for the above-described excipients.

Examples of binding agents include hydroxypropyl cellulose, hydroxypropyl methylcellulose, polyvinylpyrrolidone, macrogol and the compounds described above shown for excipients.

Examples of disintegrators include: cellulose derivatives such as hydroxypropyl cellulose with a low degree of substitutions, carboxymethyl cellulose, calcium carboxymethyl cellulose, and internally crosslinked calcium carboxymethyl cellulose; crosslinked polyvinylpyrrolidone; and chemically modified starch or cellulose derivatives such as carboxymethyl starch and sodium carboxymethyl starch.

Examples of emulsifiers include: colloidal clay such as bentonite and veegum; anionic surfactants such as sodium lauryl sulfate; cationic surfactants such as benzalkonium chloride; and non-ionic surfactants such as polyoxyethylene alkyl ether, polyoxyethylene sorbitan fatty acid ester, and sucrose fatty acid ester.

Examples of stabilizers include: para-hydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; acetic anhydride; and sorbic acid.

Examples of flavoring agents include: sweeteners such as sodium saccharin and aspartame; acidulants such as citric acid, malic acid, and tartaric acid; and flavors such as lemon extract and orange extract.

Diluents are generally compounds used as a diluent. Examples thereof include lactose, mannitol, glucose, sucrose, calcium sulfate, hydroxypropyl cellulose, microcrystalline cellulose, water, ethanol, polyethylene glycol, propylene glycol, glycerin, starch, polyvinylpyrrolidone, and mixtures thereof.

The therapeutic agent for a keratoconjunctive disorder of the present invention includes those in a form of instillation in addition to the above-described dosage forms. The agent can be formulated with a well-known method by suitably blending in an isotonizing agent, buffer, pH regulator, solubilizer, thickener, stabilizer, preservative (antiseptic) or the like as an additive. Further, it is also possible to obtain a stable instillation by adding a pH regulator, thickener, dispersant or the like to prepare suspension of a drug.

Examples of isotonizing agents include glycerin, propylene glycol, sodium chloride, potassium chloride, sorbitol and mannitol.

Examples of buffers include phosphoric acid, phosphate, citric acid, acetic acid, and ε-aminocaproic acid.

Examples of pH regulators include hydrochloric acid, citric acid, phosphoric acid, acetic acid, sodium hydroxide, potassium hydroxide, boric acid, borax, disodium hydrogen phosphate, sodium dihydrogen phosphate, sodium carbonate, and sodium bicarbonate.

Examples of solubilizers include polysorbate 80, polyoxyethylene hydrogenated castor oil 60, and macrogol 4000.

Examples of thickeners and dispersants include: cellulose polymers such as hydroxypropyl methylcellulose and hydroxypropyl cellulose; polyvinyl alcohols; and polyvinylpyrrolidone. Further, examples of stabilizers include edetic acid and sodium edetate.

Examples of preservatives (antiseptics) include commonly-used sorbic acid, potassium sorbate, benzalkonium chloride, benzethonium chloride, methyl parahydroxybenzoate, propyl parahydroxybenzoate, and chlorobutanol. It is also possible to use these preservatives in combination.

An instillation may have any pH within a range acceptable for an ophthalmic formulation, but the pH is desirably set to 4.0-8.5.

For ointments (preferably ophthalmic ointments), a commonly-used base such as white petrolatum or liquid paraffin can be used for preparation.

The dosage of the therapeutic agent for a keratoconjunctive disorder of the present invention can be appropriately changed in accordance with the dosage form, severity of symptoms of a patient to whom the agent is to be administered, age, weight, judgment of a physician or the like. For oral agents, it is generally possible to administer 0.01-5000 mg, preferably 0.1-2500 mg, and more preferably 0.5-1000 mg per day for an adult in one or several doses. For instillations, it is possible to administer those with an effective ingredient concentration of 0.000001-10% (W/V), preferably 0.00001-3% (W/V), and more preferably 0.0001-1% (W/V), in one or several daily doses. For ophthalmic ointments, it is possible to administer those with an effective ingredient concentration of 0.00001-10% (W/W), preferably 0.0001-3% (W/W), and more preferably 0.001-1% (W/W), in one or several daily doses.

Hereinafter, the present invention is explained in further detail while providing Examples (Test Examples and Formulation Examples). However, the scope of the present invention is not limited thereto.

Example 1

(Test Example) Test on Suppression of Three-Dimensional Collagen Gel Degradation in Normal Rabbit Primary Keratocytes by RARγ Agonist a Normal rabbit corneal cells were used to assess the suppression effect of a tested compound on three-dimensional collagen gel degradation in accordance with the method of Nishida et al (Investigative Ophthalmology & Visual Science 42: 1247-1253 (2001)).

Primary keratocytes collected from a normal rabbit eye ball was grown to a confluent state and detached from a culture slide with 0.05% Trypsin-EDTA. After washing in a serum free medium (product number 11095; Gibco), the number of cells were counted. The obtained primary keratocytes were mixed with the type I collagen solution Cellmatrix Type I-A (product number 637-00653; Nitta Gelatin Inc.) and Reconstitution Buffer (product number 635-00791; Nitta Gelatin Inc.) and dispensed into a 24-well plate so that the final concentration would be $1 \times 10^5$ cells/well to make a collagen gel.

After making the gel, culture was started (under conditions of 37'C and 5% $CO_2$) by adding to a MEM medium a RARγ agonist A (R667)-containing dimethyl sulfoxide solution (R667 concentration: 0.1 nM, 1 nM, 10 nM, 100 nM, or 1000 nM) or a RARγ agonist-free dimethyl sulfoxide solution as a control and 10 ng (final concentration 10 ng/ml) of IL-1β (product number 201-LB-005; R&D Systems) and 60 μg (final concentration 60 μg/ml) of Plasminogen (product number P9156; Sigma) as a stimulant, and overlaying the medium on the previously prepared collagen gel.

After 48 hours of culturing, the supernatant was ultrafiltrated, 100 μl of concentrated hydrochloric acid was added and heated, and the collagen was hydrolyzed. The reaction solution after the hydrolysis was dried under a nitrogen gas atmosphere by using a Dry Thermo Unit (DTU-2C, Taitec Co. Ltd.) and an evaporation head (E1-20 Taitec Co. Ltd.) and then dissolved in 500 μl of ultrapure water. The amount of hydroxyproline, which is the collagen degradation product in the solution, was measured in accordance with the method of Bergman et al (Analytical Chemistry 35(12): 1961-1965 (1963)) to assess the effect of suppressing collagen degradation of RARγ agonist A. The results are shown in FIG. 1.

In the present test, RARγ agonist A exhibited a dosage-dependent effect of suppressing keratoconjunctive collagen degradation.

Formulation Example (Drug Formulation Example 1) Instillation

In 100 ml

| RARγ agonist A | 100 mg |
|---|---|
| Sodium chloride | 800 mg |
| Polysorbate 80 | appropriate amount |
| Disodium hydrogen phosphate | appropriate amount |
| Sodium dihydrogen phosphate | appropriate amount |
| Sterile purified water | appropriate amount |

RARγ agonist A and the other components described above are added to sterile purified water. The solution is thoroughly mixed to prepare an instillation. It is possible to prepare an instillation with a concentration of 0.05% (W/V), 0.3% (W/V), 0.5% (W/V), or 1% (W/V) by changing the amount of RARγ agonist A or the like that is added.

(Drug Formulation Example 2) Ophthalmic Ointment

In 100 g

| RARγ agonist A | 0.3 g |
|---|---|
| Liquid paraffin | 10.0 g |
| White petrolatum | appropriate amount |

RARγ agonist A is added to homogeneously-melted white petrolatum and liquid paraffin. The mixture is thoroughly mixed and then gradually cooled to prepare an ophthalmic ointment. It is possible to prepare an ophthalmic ointment with a concentration of 0.05% (W/W), 0.1% (W/W), 0.5% (W/W), or 1% (W/W) by changing the amount of RARγ agonist A or the like that is added.

(Drug Formulation Example 3) Tablet

In 100 mg

| RARγ agonist A | 1 mg |
|---|---|
| Lactose | 66.4 mg |
| Corn starch | 20 mg |
| Calcium carboxymethyl cellulose | 6 mg |
| Hydroxypropyl cellulose | 6 mg |
| Magnesium stearate | 0.6 mg |

RARγ agonist A, corn starch and lactose are mixed in a mixer. Calcium carboxymethyl cellulose and hydroxypropyl cellulose are added to the mixture for granulation. The particle size of the resulting granules is adjusted after drying. Magnesium stearate is added to and mixed with the adjusted granules and the mixture is made into tablets with a tableting machine. Further, it is possible to prepare tablets with the content of 0.1 mg, 10 mg, or 50 mg in 100 mg by changing the amount of RARγ agonist A or the like that is added.

Example 2

(Test Example) Test on Suppression of Three-Dimensional Collagen Gel Contraction in Various Primary Cells Derived from Normal Rabbits by RARγ Agonist a Primary subconjunctival fibroblasts and primary keratocytes were used to assess the suppression effect of a tested compound on three-dimensional collagen gel contraction in accordance with the method of Nishida et al.

As in Example 1, primary subconjunctival fibroblasts were grown and detached from a culture slide. After washing, a cell suspension was made. The resulting suspension ($1.1 \times 10^7$ cells/well MEM), type I collagen solution (5 mg/ml), 10×MEM, Reconstitution Buffer, and water were mixed on ice at 0.2:7:1:1:1.8 (volume ratio). A culture dish coated with 1% BSA was inoculated with 0.5 ml of the mixture, which was incubated for one hour at 37° C. to make a collagen gel.

Then, 0.5 ml of serum free media, to which a certain amount (1 ng/ml) of TGF-β1 (R&D Systems) and RARγ agonist A at each of the concentrations 1 nM, 10 nM, and 100 nM were added, were each added onto the above-described gel. The gel, together with a gel to which an agent-free serum-free medium was added, was continuously incubated at 37° C. The diameter of gels was measured from the time when 24 hours has past. The results of measuring the diameters of the gels after 48 hours are shown in FIG. 2.

The gel diameter was measured for primary keratocytes in a similar manner to the primary subconjunctival fibroblasts. The results are shown in FIG. 3.

Figure 2:
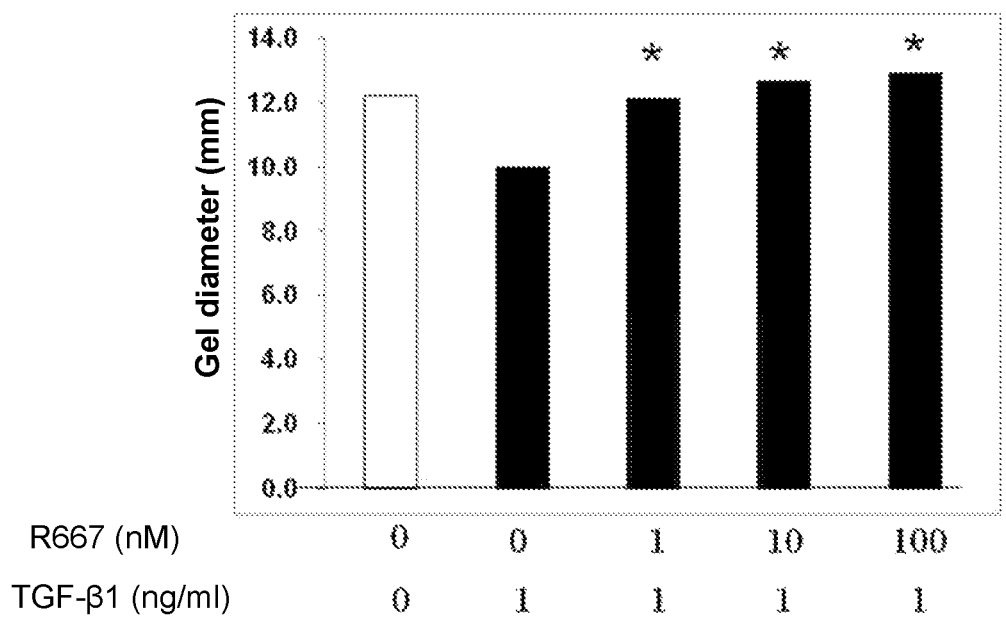
FIG. 2 is a graph showing the relationship between the concentration (nM) of RARγ agonist A (R667) and collagen contraction (diameter (mm) of collagen gel in the dish) when using subconjunctival fibroblasts, wherein "*" indicates the presence of a statistically significant difference ($p<0.05$).
Figure 3:
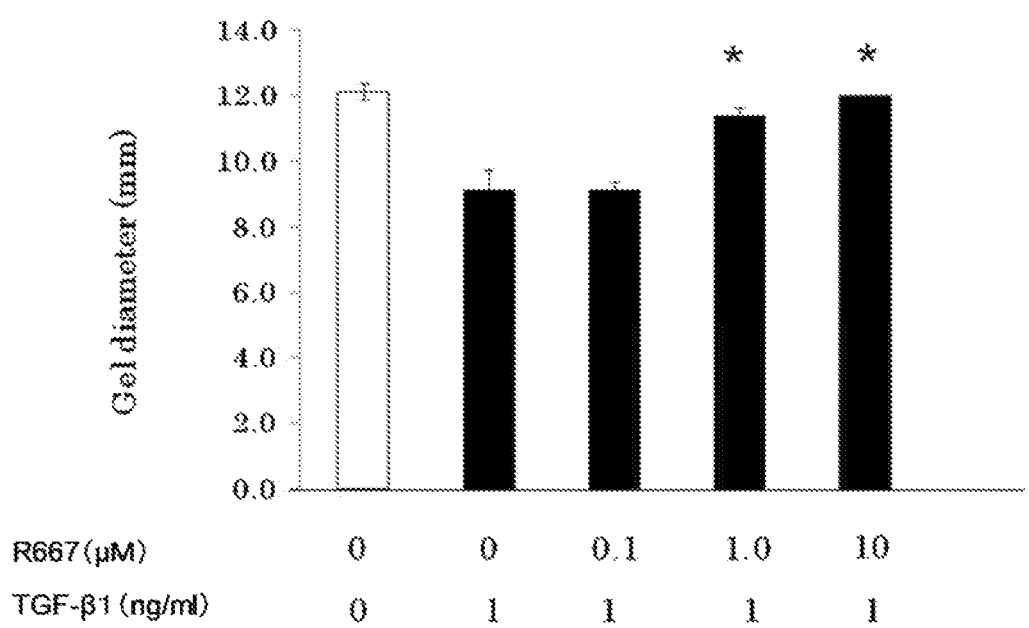
FIG. 3 is a graph showing the relationship between the concentration (μM) of RARγ agonist A (R667) and collagen contraction (diameter (mm) of collagen gel in the dish) when using keratocytes, wherein "*" indicates the presence of a statistically significant difference ($p<0.05$).

It can be seen from FIGS. 2 and 3 that RARγ agonist A not only can suppress collagen degradation, but also collagen gel contraction due to TGF using subconjunctival fibroblasts or keratocytes. This demonstrates that RARγ agonist A contributes to collagen turn over and has an effect of suppressing tissue remodeling that occurs after inflammation, hemorrhage, infection, surgery, or injury in an ophthalmic tissue, i.e., fibrillation or cicatrization.

Example 3

(Test Example) Test on Suppression of Three-Dimensional Collagen Gel Degradation in Primary Keratocytes Derived from Normal Rabbits by RARγ Agonist a, B, or C Primary keratocytes were used to assess the suppression effect of a tested compound on three-dimensional collagen gel degradation by the same method as in Example 1 in accordance with the method of Nishida et al.

As in Example 1, primary keratocytes were grown and detached from a culture slide. After washing, a cell suspension was made. The resulting suspension ($1.1 \times 10^7$ cells/well MEM), type I collagen solution (5 mg/ml), 10×MEM, Reconstitution Buffer, and water were mixed on ice at 0.2:7:1:1:1.8 (volume ratio). A culture dish coated with 1% BSA was inoculated with 0.5 ml of the mixture, which was incubated for one hour at 37° C. to make a collagen gel.

After making the gel, culture was started (under conditions of 37° C. and 5% $CO_2$) by adding to a MEM medium a RARγ agonist A (R667)-containing dimethyl sulfoxide solution (1 nM), RARγ agonist B (CD437)-containing dimethyl sulfoxide solution (1 nM, 10 nM), RARγ agonist C (BMS961)-containing dimethyl sulfoxide solution (10 nM), or a RARγ agonist-free dimethyl sulfoxide solution as a control, and 10 ng (final concentration 10 ng/ml) of IL-113 (product number 201-LB-005; R&D Systems) and 60 µg (final concentration 60 µg/ml) of Plasminogen (product number P9156, Sigma Aldrich) as a stimulant, and overlaying the medium on the previously prepared collagen gel.

After 48 hours of culturing, collagen was hydrolyzed and the amount of hydroxyproline, which is the collagen degradation product, was measured by the same method as Example 1 to assess the effect of suppressing collagen degradation of each RARγ agonist. The results are shown in FIG. 4.

In the present test, not only RARγ agonist A, but also RARγ agonists B and C exhibited an effect of suppressing keratoconjunctive collagen degradation.

Example 4

(Test Example) Test on Suppression of the Expression and Activation of MMP-1, 2, 3, and 9 by RARγ Agonist a It is believed that secretion or expression of protease, i.e., matrix metalloproteinases (MMP), is associated with the degradation of type I collagen. In this regard, suppression of expression and activation of MMP-1, 2, 3, and 9 by RARγ agonist A was investigated.

Primary keratocytes collected from a normal rabbit eye ball were cultured for 24 hours in a serum-free MEM medium. RARγ agonist A (R667) (R667 concentration: $1 \times 10^{-6}$ µM, $1 \times 10^{-5}$ µM, $1 \times 10^{-4}$ µM, $1 \times 10^{-3}$ µM, $1 \times 10^{-2}$ µM) was added to the obtained culture solution and 12 hours of pre-treatment was performed. As a positive control, 10 nM of dexamethasone (Dex), which is a synthetic steroid, was added and pre-treatment was similarly performed. Then, IL-1β (0.1 ng/ml) was added for stimulation, and the supernatant was collected after 24 hours. The following western blot analysis and gelatin zymography analysis were used on the collected culture solution.

(Western Blot Analysis)

After developing the supernatant of the collected culture solution in SDS-PAGE using 10% polyacrylamide gel, the separated proteins were transferred onto a nitrocellulose filter. Then, non-specific sites on the nitrocellulose filter were blocked and incubated for 24 hours at 4° C. with anti-human MMP-1 antibodies (R&D Systems) and anti-rabbit MMP-3 antibodies (Daiichi Fine Chemical Co., Ltd). ECL® reagent (GE Healthcare) was used for detection.

Figure 5A:
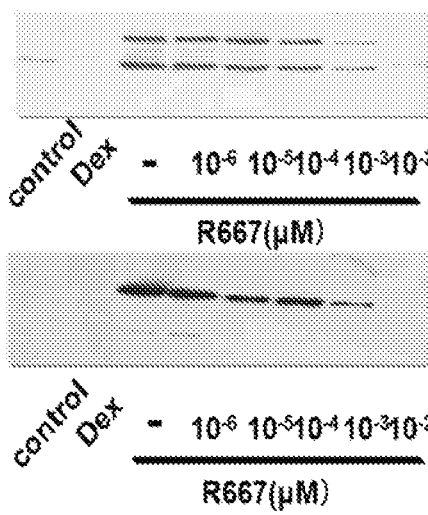
FIGS. 5A and 5B show the relationship between the concentration (μM) of RARγ agonist A (R667) and the expression and activation of matrix metalloproteinases (MMP) when using keratocytes. The top row of FIG. 5A shows the expression and activation of MMP-1, the bottom row of FIG. 5A shows the expression and activation of MMP-3.

The results are shown in FIG. 5A. The band for each of the non-active Pro-MMP-1, Pro-MMP-3 and active MMP-1, MMP-3 was diminished, where the extent thereof was dependent on the concentration of RARγ agonist A. Thus, it was revealed that RARγ agonist A concentration-dependently suppresses the expression and activation of MMP-1 and MMP-3.

(Gelatin Zymography Analysis)

After developing the supernatant of the collected culture solution on SDS-PAGE using 10% polyacrylamide gel containing 0.1% of gelatin, it was incubated for one hour at room temperature with a TBS solution containing 2.5% Triton X-100. The gel after incubation was dyed with a solution of Coomassie Brilliant Blue (Wako Pure Chemical Industries, Ltd.) and decolored with a 5% methanol-7.5% acetic acid solution (Nacalai Tesque, Inc).

Figure 5B:
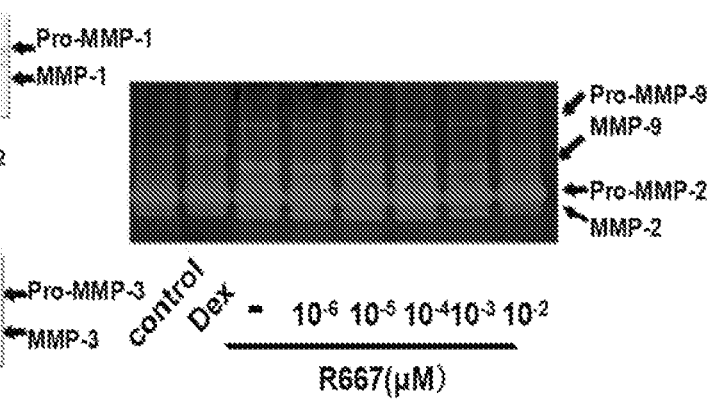

The results are shown in FIG. 5B. The band for each of the non-active Pro-MMP-2, Pro-MMP-9 and active MMP-2, MMP-9 was diminished, where the extent thereof was dependent on the concentration of RARγ agonist A. Thus, it was revealed that RARγ agonist A concentration-dependently suppresses the expression and activation of MMP-2 and MMP-9.

Example 5

(Test Example) Test on Suppression of Corneal Opacity and Ulceration with RARγ Agonist a Systemic anesthesia was applied to male Japanese white rabbits (body weight 2.5-3.5 kg, 27 rabbits) by intramuscular administration of a solution of a mixture of ketamine and xylazine. Then, topical anesthesia was applied by a 0.4% oxybuprocaine hydrochloride instillation. Furthermore, 30 µl of 1% LPS (Sigma Aldrich) was injected into the corneal stroma of one eye, but not in the other eye.

Figure 6A:
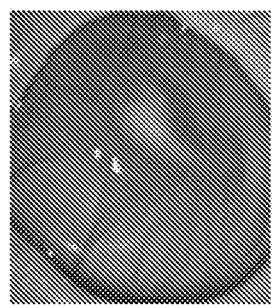
[FIGS. 6A and 6B]
Figure 6B:
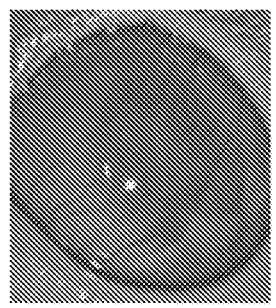

50 µl of 0.1% PBS/0.1% polysorbate 80 solution containing RARγ agonist A (R667: 0.1%, 24 mM) was instillatively administered to the rabbits injected with LPS twice after the injection on the day of LPS injection and four times daily thereafter until day 10 by using a micropipette. As a control, a 0.1% PBS/0.1% polysorbate 80 solution free of RARγ agonist A (Vehicle) was similarly administered. FIGS. 6A and 6B show representative examples of a control and a case where RARγ agonist A was administered.

In FIGS. 6A and 6B, corneal opacity and ulceration were observed in the control (Vehicle) shown in the top row (FIG. 6A). However, in a case where RARγ agonist A was administered (0.1% R667) shown in the bottom row (FIG. 6B), corneal opacity and ulceration were not observed. Thus, it was revealed that RARγ agonist A suppresses corneal opacity and ulceration.

INDUSTRIAL APPLICABILITY

RARγ agonists, which are effective ingredients of the therapeutic agent for a keratoconjunctive disorder of the present invention, are useful in preventing or as a therapeutic agent for keratoconjunctive disorders, such as corneal ulcer, corneal epithelial abrasion, keratitis, dry eye, conjunctivitis, chronic superficial keratitis, corneal erosion, persistent corneal disorders, superficial punctate keratopathy, corneal epithelial defects, conjunctival epithelial defects, keratoconjunctivitis, superior limbic keratoconjunctivitis, filamentary keratoconjunctivitis, infectious keratitis, noninfectious keratitis, infectious conjunctivitis and noninfectious conjunctivitis, by strongly suppressing collagen degradation. Further, said RARγ agonists are also useful as a therapeutic agent for corneal cicatrization or conjunctival cicatrization associated with a keratoconjunctive disorder by strongly suppressing collagen contraction.

The invention claimed is:

1. A method of preventing or treating keratitis in a subject in need thereof, comprising administering to the subject an RARγ agonist, or an ester or salt thereof, in an amount effective to prevent or treat keratitis, wherein said RARγ agonist is (E)-4-(2-{3-[(1H-pyrazole-1-yl)methyl]-5,5,8,8-tetramethyl-5,6,7,8-tetrahydronaphthalene-2-yl}vinyl)benzoic acid (R667), 6-[3-(1-adamantyl)-4-hydroxyphenyl]-2-naphthalene acid (CD437), 3-fluoro-4-[2-hydroxy-2-(5,5,8,8-tetramethyl-5,6,7,8-tetrahydronaphthalene-2-yl)acetylamino]benzoic acid (BMS961), (2E)-3-(4-carboxyphenyl)-1-(5,5,8,8-tetramethyl-5,6,7,8-tetrahydronaphthalene-2-yl)-2-propene-1-one oxime (NRX204647), 4-[7-(1-adamantyl)-6-hydroxynaphthalene-2-yl] benzoic acid (CD1530), an ester thereof, or a salt thereof.

2. The method of claim 1, wherein corneal opacity is suppressed.

3. The method of claim 1, wherein corneal damage or scarring is inhibited.

4. The method of claim 1, wherein said RARγ agonist is (E)-4-(2-{3-[(1H-pyrazole-1-yl)methyl]-5,5,8,8-tetramethyl-5,6,7,8-tetrahydronaphthalene-2-yl}vinyl)benzoic acid (R667), an ester thereof, or a salt thereof.

5. The method of claim 1, wherein said RARγ agonist is 6-[3-(1-adamantyl)-4-hydroxyphenyl]-2-naphthalene acid (CD437), 3-fluoro-4-[2-hydroxy-2-(5,5,8,8-tetramethyl-5,6,7,8-tetrahydronaphthalene-2-yl)acetylamino]benzoic acid (BMS961), (2E)-3-(4-carboxyphenyl)-1-(5,5,8,8-tetramethyl-5,6,7,8-tetrahydronaphthalene-2-yl)-2-propene-1-one oxime (NRX204647), 4-[7-(1-adamantyl)-6-hydroxynaphthalene-2-yl] benzoic acid (CD1530), an ester thereof, or a salt thereof.

6. The method of claim 1, wherein the RARγ agonist is in the form of a powder, syrup, granule, liquid formulation, suspension, emulsion, ointment, or instillation.

7. The method of claim 6, wherein the ointment is an ophthalmic ointment.

8. The method of claim 7, wherein the ointment comprises a solubilizer.

9. The method of claim 8, wherein the solubilizer is selected from the group consisting of polysorbate 80, polyoxyethylene hydrogenated castor oil 60, and macrogol 4000.

10. The method of claim 9, wherein the solubilizer is polysorbate 80.

11. The method of claim 7, wherein the concentration of the RARγ agonist in the ophthalmic ointment is from 0.0001% to 3% (w/w) or from 0.001% to 1% (w/w).

12. The method of claim 6, wherein the RARγ agonist is in the form of a liquid formulation.

13. The method of claim 12, wherein the liquid formulation comprises a solubilizer.

14. The method of claim 13, wherein the solubilizer is selected from the group consisting of polysorbate 80, polyoxyethylene hydrogenated castor oil 60, and macrogol 4000.

15. The method of claim 14, wherein the solubilizer is polysorbate 80.

16. The method of claim 12, wherein the concentration of the RARγ agonist in the liquid formulation is from 0.00001% to 3% (w/v), from 0.0001% to 1% (w/v), 0.3% (w/v), 0.5% (w/v), or 1% (w/v).

17. The method of claim 1, wherein the RARγ agonist is ocularly administered to the subject in one or more daily doses.

18. The method of claim 1, wherein the administering is administering by instillation.

19. The method of claim 1, wherein the keratitis is chronic superficial keratitis, infectious keratitis, or noninfectious keratitis.

* * * * *